United States Patent
Hu et al.

(10) Patent No.: US 12,128,111 B2
(45) Date of Patent: Oct. 29, 2024

(54) GLYCO-METAL-ORGANIC FRAMEWORKS-BASED HEPATIC TARGETED THERAPEUTIC DRUG AND PREPARATION METHOD THEREOF

(71) Applicant: Jiangnan University, Wuxi (CN)

(72) Inventors: Jing Hu, Wuxi (CN); Jian Yin, Wuxi (CN); Jun Hu, Wuxi (CN)

(73) Assignee: Jiangnan University, Wuxi (CN)

( * ) Notice: Subject to any disclaimer, the term of this patent is extended or adjusted under 35 U.S.C. 154(b) by 769 days.

(21) Appl. No.: 17/345,582

(22) Filed: Jun. 11, 2021

(65) Prior Publication Data

US 2021/0308280 A1   Oct. 7, 2021

Related U.S. Application Data

(63) Continuation of application No. PCT/CN2020/097638, filed on Jun. 23, 2020.

(30) Foreign Application Priority Data

Dec. 13, 2019   (CN) .......................... 201911280230.7

(51) Int. Cl.
| | |
|---|---|
| *C07H 1/00* | (2006.01) |
| *A61K 31/44* | (2006.01) |
| *A61K 31/513* | (2006.01) |
| *A61K 31/704* | (2006.01) |
| *A61K 41/00* | (2020.01) |
| *A61K 47/54* | (2017.01) |
| *A61K 47/60* | (2017.01) |
| *A61K 47/69* | (2017.01) |

(52) U.S. Cl.
CPC .......... *A61K 47/6949* (2017.08); *A61K 31/44* (2013.01); *A61K 31/513* (2013.01); *A61K 31/704* (2013.01); *A61K 41/0071* (2013.01); *A61K 47/546* (2017.08); *A61K 47/549* (2017.08); *A61K 47/60* (2017.08); *C07H 1/00* (2013.01)

(58) Field of Classification Search
None
See application file for complete search history.

(56) References Cited

FOREIGN PATENT DOCUMENTS

| CN | 101259284 A | * | 9/2008 |
| CN | 108517038 A | | 9/2018 |
| CN | 110898223 A | | 3/2020 |

OTHER PUBLICATIONS

Zhang et al., Inorg. Chem, 2019, 58, 6593-6596. (Year: 2019).*

* cited by examiner

*Primary Examiner* — Traviss C Mcintosh, III
(74) *Attorney, Agent, or Firm* — IPRO, PLLC; Na Xu

(57) ABSTRACT

The disclosure discloses a glyco-metal-organic frameworks-based hepatic targeted therapeutic drug and a preparation method thereof, and belongs to the field of biomedicine. The disclosure loads a chemotherapeutic drug onto specific metal-organic frameworks, and modifies targeted molecule galactose on the surface of the materials through amide reaction. The biocompatibility and cytotoxicity of the obtained hepatic targeted therapeutic drug have been carefully evaluated at the cellular level. The hepatic targeted therapeutic drug of the disclosure has good stability and acidic pH triggered drug release property, and can exert the synergistic therapeutic effect of photodynamic therapy and chemotherapy. In addition, in vivo behavioral tracing and therapeutic efficacy are evaluated in mouse models with subcutaneous solid tumor and tumor in situ, and the disclosure is expected to play a huge role in clinical applications.

8 Claims, 15 Drawing Sheets

GLYCO-METAL-ORGANIC FRAMEWORKS-BASED HEPATIC TARGETED THERAPEUTIC DRUG AND PREPARATION METHOD THEREOF

TECHNICAL FIELD

The disclosure relates to a glyco-metal-organic frameworks-based hepatic targeted therapeutic drug and a preparation method thereof, and belongs to the field of biomedicine.

BACKGROUND

Primary hepatic carcinoma, mainly hepatocellular carcinoma (HCC), has an insidious onset, and is difficult in early diagnosis, rapid in progress, difficult in treatment and dangerous in prognosis. The incidence of HCC ranks 6th among global malignant tumors, and the mortality rate ranks 2nd. More than half of the new cases and deaths are from China. In 2016, a high-quality population-based epidemiological survey of the National Cancer Registration Center collected and analyzed data from 72 registration points (covering 6.5% of China's population) and showed that the number of new cases of hepatic carcinoma in China was 466,000 and the number of deaths was 422,000. Hepatic carcinoma is the most common malignant tumor with the highest mortality rate among men under 60 in China. Cirrhosis caused by chronic hepatitis B, alcoholism or hepatitis C infection is the main risk factor for HCC, followed by non-alcoholic steatohepatitis. The incidence of HCC is higher in areas where hepatitis B virus (HBV) is endemic, including China, Southeast Asia, and sub-Saharan Africa, while chronic hepatitis C virus (HCV), alcoholic cirrhosis and non-alcoholic steatohepatitis are the main reasons for Western people suffering from HCC. Based on this, the treatment of hepatic carcinoma has attracted more and more attention worldwide. Radical treatments such as surgical resection, liver transplantation, or radiofrequency ablation are only suitable for less than 30% of cases. Sorafenib is the first-line therapeutic drug for patients with advanced HCC, but with the occurrence of high-frequency adverse events, the overall survival rate has not been significantly improved. In addition, most of the existing drugs are free small-molecule drugs, which are distributed throughout the body after administration, and cannot accumulate in the lesion. Therefore, the curative effect is limited and the toxic and side effects on the patient are large.

SUMMARY

In order to solve the problems, the disclosure uses nano-scale metal-organic frameworks as a drug carrier, and is modified with sugar molecule targeting groups, so that the passive targeting of nanomaterials and the active targeting of sugar-based materials are combined together, and can well aggregate at the lesion site to achieve a targeted therapeutic effect. The disclosure overcomes the current problem that sugar molecules as polyhydroxy aldehyde structures are not easily modified to the surface of nanomaterials. The sugar molecules are chemically modified, their terminal group sites are linked to amino linking arms, and the sugar molecules are covalently linked to the outside of the metal-organic frameworks through amide reaction, thereby achieving the targeting effect.

The disclosure further realizes concentration of multiple functions in a nanomaterial carrier, and provides a new type of treatment system that integrates a photosensitizer and a chemotherapeutic drug into a carrier with good biocompatibility and safety. First, metal-organic frameworks PCN-224 with porphyrin as the linking arm are used as a carrier to load the anti-tumor drug doxorubicin DOX (named DOX@PCN-224), thereby realizing synergistic treatment of photodynamic therapy and chemotherapy. Subsequently, the surface of the DOX@PCN-224 is modified with COOH-PEG-COOH by electrostatic adsorption, thereby introducing carboxyl groups on the surface of DOX@PCN-224. Finally, the surface of the material is modified with galactose targeting molecules through amide reaction, thereby successfully forming a targeted synergistic treatment nano-system.

An objective of the disclosure is to provide a drug of combined photodynamic therapy and chemotherapy and acid-sensitive tracing for targeted treatment of hepatic diseases. The structure of the drug has components A, B, C and D;

A is selected from one or more of the same or different chemotherapeutic drugs: doxorubicin (DOX), sorafenib and 5-fluorouracil (5-FU);

B is metal-organic frameworks (MOFs) with a photosensitizer as a linking arm;

C is a linking group, and the linking group is -CO-PEG-CO-; the molecular weight of PEG is 1000-2000; and D is galactose or a monosaccharide or oligosaccharide molecule containing a galactosamine residue, and is capable of specifically recognizing an asialoglycoprotein receptor overexpressed on the surface of hepatic carcinoma cells.

In one example of the disclosure, the metal-organic frameworks (MOFs) are selected from PCN-224 and PCN-222.

The CAS number of the PCN-224 is 1476810-88-4. The CAS number of the PCN-222 is CAS: 1403461-06-2.

In one example of the disclosure, the drug is abbreviated as chemotherapeutic drug@Gal-MOFs.

Another aspect of the disclosure is to provide a method for preparing the drug of Formula (I), including the following steps:

(1) Preparation of DOX@-PCN-224 dispersing $ZrOCl_2 \cdot 8H_2O$, TCPP and benzoic acid in an organic solvent; mixing the materials uniformly; adding doxorubicin to form a mixed system; performing reaction at 80-100° C.; then performing solid-liquid separation to collect precipitate; washing and drying the precipitate to obtain DOX@PCN-224;

(2) dispersing the DOX@PCN-224 obtained in the step (1) and COOH-PEG-COOH in water to form a mixed solution; performing reaction at room temperature; after the reaction, performing solid-liquid separation to collect precipitate; washing and drying the precipitate to obtain carboxyl-modified DOX@PCN-224; and (3) dissolving the carboxyl-modified DOX@PCN-224 obtained in the step (2), amino-modified galactose, and a condensing agent in water; performing reaction at room temperature; after the reaction, performing solid-liquid separation to collect precipitate; washing and drying the precipitate to obtain DOX@Gal-PCN-224.

In one example of the disclosure, the mass ratio of the doxorubicin to the $ZrOCl_2 \cdot 8H_2O$ to the TCPP to the benzoic acid in the step (1) is 1:(5-8):(2-4):(50-60), preferably 1:6.25:2.08:58.33.

In one example of the disclosure, the organic solvent in the step (1) is DMF.

In one example of the disclosure, the concentration of the doxorubicin in the mixed system in the step (1) is 0.4-0.6 mg/mL, preferably 0.44 mg/mL.

In one example of the disclosure, the mass ratio of the DOX@PCN-224 to the COOH-PEG-COOH in the step (2) is (2-2.5): 1, preferably 2:1.

In one example of the disclosure, the mass concentration of the DOX@PCN-224 in the mixed solution in the step (2) is 0.8-1.2 mg/mL, preferably 0.9 mg/ml.

In one example of the disclosure, in the step (3), the mass ratio of the carboxyl-modified DOX@PCN-224 to the amino-modified galactose is 1:(0.5-0.8), preferably 1:0.67.

In one example of the disclosure, the condensing agent in the step (3) contains 1-(3-dimethylaminopropyl)-3-ethylcarbodiimide hydrochloride (EDC·HCl) and N-hydroxysuccinimide (NHS).

In one example of the disclosure, the mass ratio of the 1-(3-dimethylaminopropyl)-3-ethylcarbodiimide hydrochloride to the N-hydroxysuccinimide in the condensing agent is 1.7:1.

Beneficial Effects

The drug of the disclosure integrates the properties of hepatic tumor tissue targeting and tracing. The biocompatibility and cytotoxicity of the drug of the disclosure have been carefully evaluated. The stability and the acidic pH triggered drug release property of the targeted synergistic treatment nanosystem are studied in vitro. Moreover, drug delivery, singlet oxygen generation capacity, and the synergistic therapeutic effect of photodynamic therapy and chemotherapy are studies in both HepG2 and Huh7 cell lines. In addition, in vivo behavioral tracing and therapeutic efficacy are evaluated in mouse models with subcutaneous solid tumor and tumor in situ, and excellent tracing and therapeutic effects are achieved.

BRIEF DESCRIPTION OF FIGURES

FIG. 1A Scanning electron micrograph of an inorganic nanomaterial DOX@Gal-PCN-224; FIG. 1B Transmission electron micrograph of the inorganic nanomaterial DOX@Gal-PCN-224; FIG. 1C Scanning electron microscopy element mapping C—K, N—K, O—K and Zr—K signals; FIG. 1D Ultraviolet-visible absorption spectrum analysis: (a) DOX@PCN-224, (b) COOH-PEG-COOH modified DOX@PCN-224 and (c) DOX@Gal-PCN-224; and FIG. 1E Hydrodynamic size distribution diagram of the inorganic nanomaterial DOX@Gal-PCN-224.

FIG. 9A In vivo images at different time points after tail vein injection of the DOX@Gal-PCN-224-RhB and the DOX@PCN-224-RhB; and FIG. 9B Images of isolated organs at different time points.

FIG. 10A Growth curves of mouse tumors in different treatment groups (the arrows indicate photodynamic treatment time); FIG. 10B Photos of tumor tissues peeled off after 21 days of treatment in the treatment groups: (a) Saline, (b) DOX, (c) DOX+light, (d) PCN-224, (e) PCN-224+light, (f) DOX@PCN-224, (g) DOX@PCN-224+light, (h) DOX@Gal-PCN-224 and (i) DOX@Gal-PCN-224+light.

FIG. 11A T1-weighted images of livers in each experimental group: (a) Saline, (b) DOX, (c) DOX+light, (d) PCN-224, (e) PCN-224+light, (f) DOX@PCN-224, (g) DOX@PCN-224+light, (h) DOX@Gal-PCN-224 and (i) DOX@Gal-PCN-224+light (white dotted circles represent tumor sites); and FIG. 11B Photos of liver tissues with tumors removed after 21 days of treatment in each experimental group: (a) Saline, (b) DOX, (c) DOX+light, (d) PCN-224, (e) PCN-224+light, (f) DOX@PCN-224, (g) DOX@PCN-224+light, (h) DOX@Gal-PCN-224 and (i) DOX@Gal-PCN-224+light (white dotted circles represent tumor sites), the scale bar being 5 mm.

DETAILED DESCRIPTION

The implementation plan of the disclosure will be described in detail below with reference to the examples, but those skilled in the art will understand that the following examples are intended to illustrate the disclosure and are not to be considered as limiting the scope of the disclosure. Those which are not specified with specific conditions in the examples are carried out according to conventional conditions or conditions recommended by manufacturers. Any reagents or instruments that are not indicated with the manufacturers are commercially available products.

Example 1: Preparation of Drug DOX@Gal-PCN-224

10 mL of DMF solution of $ZrOCl_2·8H_2O$ (15 mg/mL), 20 mL of DMF solution of TCPP (2.5 mg/mL) and 20 mL of DMF solution of benzoic acid (70 mg/mL) were added into a round-bottom flask respectively. 4 mL of aqueous solution of doxorubicin (6 mg/ml) was added into the round-bottom flask while stirring. The mixed solution was then stirred at 90° C. for 5 hours, and then precipitate was collected by centrifugation and washed with DMF and water three times respectively. Finally, the precipitate was dried in a vacuum drying oven to obtain a powder product DOX@PCN-224.

The obtained product DOX@PCN-224 was dissolved in water to prepare a 1 mg/ml aqueous solution. 20 ml of aqueous solution of DOX@PCN-224 and 2 mL of aqueous solution of COOH-PEG-COOH (5 mg/mL, and $M_w$ of the COOH-PEG-COOH=1K, 2 mL) were added to the round-bottom flask. The mixed solution was stirred at room temperature for 4 hours, and then precipitate was collected by centrifugation and washed with water three times. Finally, the precipitate was dried in a vacuum drying oven to obtain carboxyl-modified DOX@PCN-224.

The carboxyl-modified DOX@PCN-224 (15 mg), amino-modified galactose (10 mg), 1-(3-dimethylaminopropyl)-3-ethylcarbodiimide hydrochloride (EDC·HCl, 17 mg) and N-hydroxysuccinimide (NHS, 10 mg) were dissolved in 10 ml of water, and the mixed solution was stirred at room temperature for 48 hours. Then precipitate was collected by centrifugation and washed with water three times. Finally, the precipitate was dried in a vacuum drying oven to obtain a powder product DOX@Gal-PCN-224. The drug loading ratio of DOX is 14.2%. (Drug loading ratio=total amount of DOX loaded/total amount of material product)

Example 2: Characterization of DOX@Gal-PCN-224

The particle size distribution of the DOX@Gal-PCN-224 prepared in Example 1 was characterized by scanning electron microscopy (SEM), transmission electron microscopy (TEM), transmission electron microscopy element analysis, scanning electron microscopy element mapping, ultraviolet-visible absorption spectrum analysis and dynamic light scattering technology.

It can be seen from FIG. 1A-1E that the prepared DOX@Gal-PCN-224 is uniformly distributed spherical nanoparticles with a particle size of 121 nm.

Figure 1A:
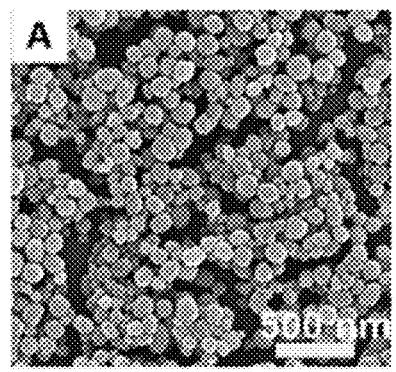
FIG. 1A-1E shows.
Figure 1B:
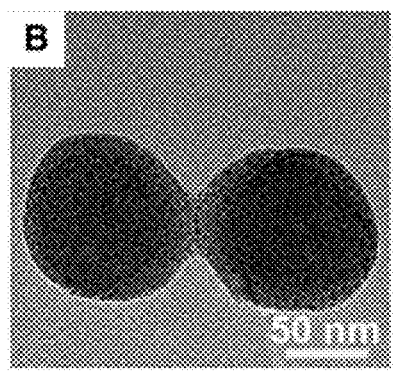
Figure 1C:
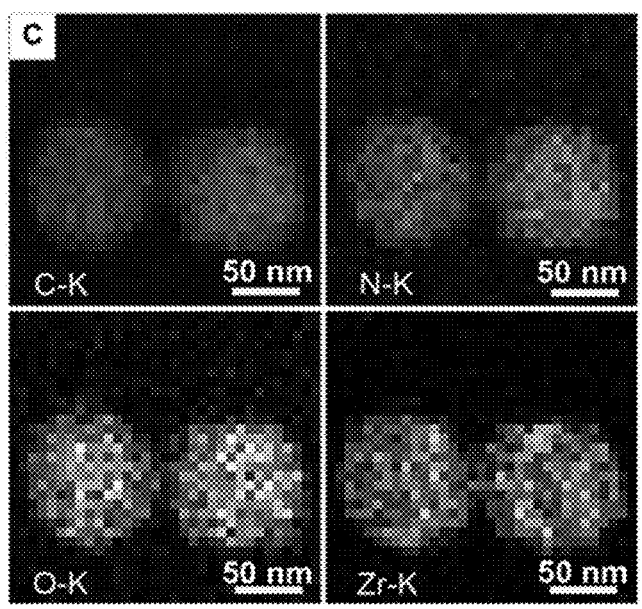
Figure 1D:
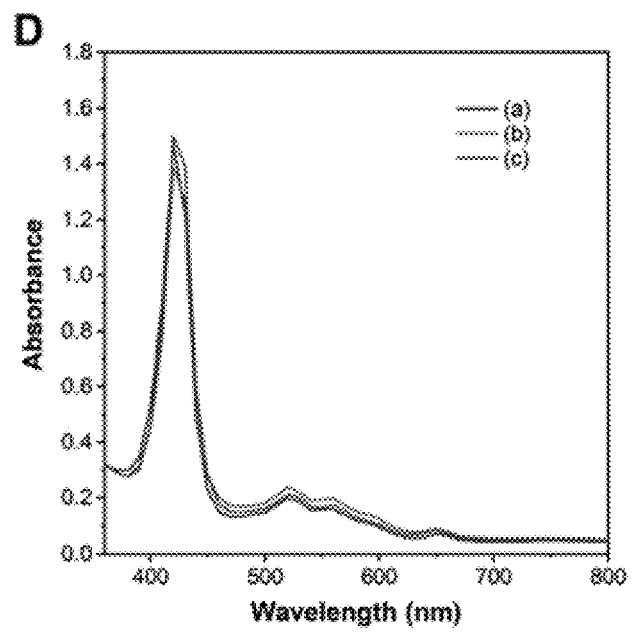
Figure 1E:
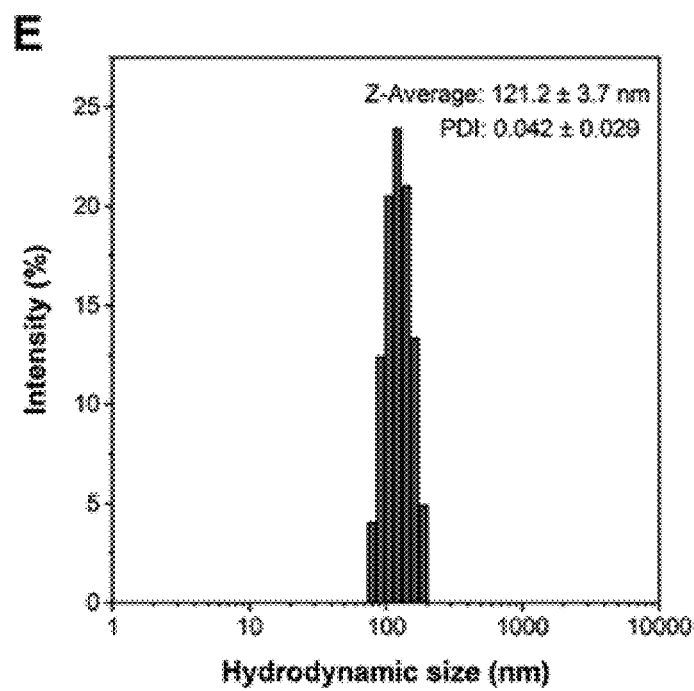
Figure 2:
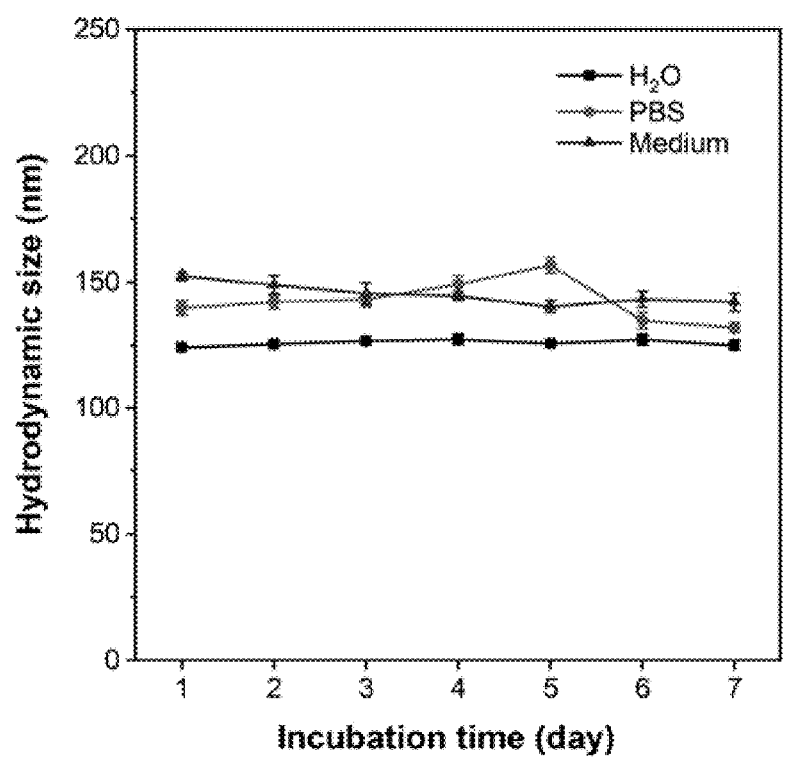
FIG. 2 shows the stability of the DOX@Gal-PCN-224 hydrodynamic size in the presence of water, a PBS buffer (pH 7.4) and a medium containing 10% FBS.

The stability of materials is an important prerequisite for the application of materials in biomedicine. It can be seen from FIG. 2 that after the inorganic nanomaterial was incubated with water, a phosphate buffer solution (PBS) with pH of 7.4 and a medium containing 10% fetal bovine serum for 7 days, the particle size had no significant change, and it proves that the inorganic nanomaterial has good stability.

Example 3: Acid-sensitive release of DOX@Gal-PCN-224

10 mg of inorganic nanomaterial DOX@Gal-PCN-224 was placed in 20 ml of PBS buffer solutions with pH 7.4 and 5.6, respectively. The mixture was stirred at 37° C. Supernate was taken at a fixed time point to measure the absorbance at 480 nm. Then the sample was returned to an original release system. The release percentage of the DOX was calculated according to the formula: release percentage (%)=$m_r/m_t$, where $m_r$ is the amount of DOX released and $m_t$ is the total amount of DOX loaded (1.42 mg).

Figure 3:
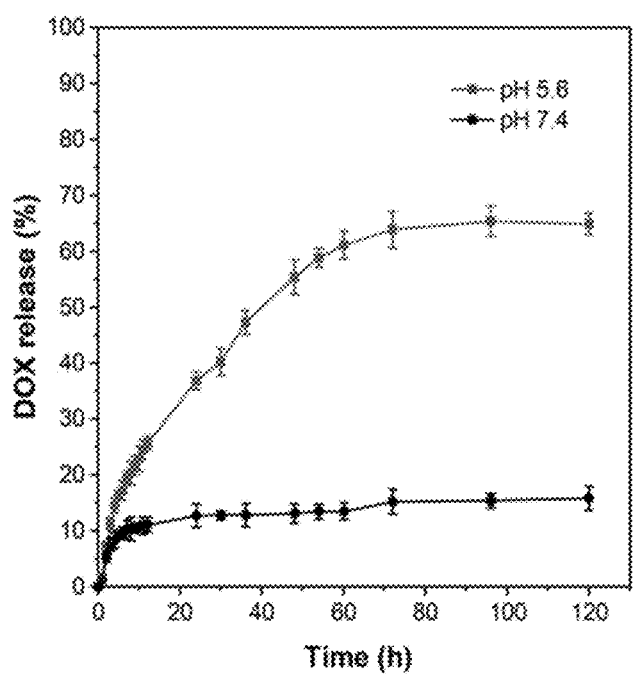
FIG. 3 shows the release curves of the inorganic nanomaterial DOX@Gal-PCN-224 under different pH conditions.

The release results are shown in FIG. 3. The inorganic nanomaterial remains stable under an imitated physiological condition (pH 7.4), and slightly releases 15.8% of DOX after being incubated for 120 hours. Under an acidic condition (pH 5.6), the release rate of DOX is relatively fast (being 25.7% after 12 hours, 55.4% after 48 hours, and 65.0% after 120 hours). Therefore, drug delivery based on DOX@Gal-MOF can be used for the targeted treatment of tumors with DOX release in response to pH.

Example 4: Experiment of Cytotoxicity of DOX@Gal-PCN-224

Human hepatoma cells HepG2 and Huh7, and human embryonic kidney cells HEK293 were inoculated on a 96-well plate at the density of $8 \times 10^3$ per well. After being incubated for 48 hours, the cells grew steadily in the well plate, and the inorganic nanomaterial DOX@Gal-PCN-224 in Example 1 was added to each of wells at the concentration of 0, 10, 20, 40, 60, 80, 100 and 120 µg/mL respectively. After the materials and the cells were co-incubated for 48 hours, the medium was removed. The cells were washed three times with PBS. Then 100 µL of medium containing 0.5 mg/mL MTT without addition of phenol red was added into each well, and then 100 µL of DMSO was added into each well. For the developed 96-well plate, the absorbance values ($\lambda$=490 nm) of all wells in the plate were detected using a microplate reader. Six parallel experiments were repeated for each sample. The cell group not subjected to the effect of the material was defined to have 100% cell viability, and the well with only the DMSO solution but no cells was defined as a blank control to correct the absorbance values in each well.

Figure 4:
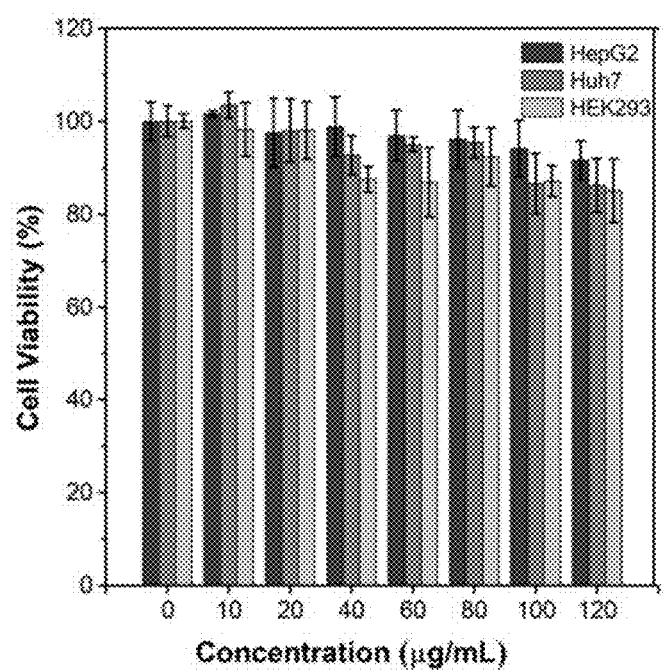
FIG. 4 shows the cell viability of HepG2, Huh7 and HEK293 cells incubated with the Gal-PCN-224 of various concentrations for 48 hours.

FIG. 4 shows the results of the cytotoxicity of the inorganic nanomaterial DOX@Gal-PCN-224. The results show that, in the concentration range of the inorganic nanomaterial in Example 1 of 0-120 µg/mL, the survival rate of the three kinds of cells is greater than 80%, and it indicates that the inorganic nanomaterial has low toxicity and good biocompatibility.

Example 5: Verification of Capability of Drug DOX@Gal-PCN-224 of Specifically Targeting and Recognizing Asialoglycoprotein Receptors on Surfaces of Hepatoma Cells HepG2 and Huh7 by Laser Confocal Experiment Human hepatoma cells HepG2 and Huh7, and human embryonic kidney cells HEK293 were respectively inoculated in a laser confocal culture dish (35 mm) at the density of $8 \times 10^4$ per well. After culturing for 12 hours, 1 mM of galactose was added in a galactose competition group. After culturing for 24 hours, the medium was removed and the cells were washed three times with PBS. Then a medium containing 20 µg/mL DOX@Gal-PCN-224 was added and incubated for 3 hours. The medium was removed and the cells were washed three times with PBS. Then 4% paraformaldehyde was added for immobilization at room temperature for 15 min. Then nuclei were stained with 4',6-diamidino-2-phenylindole (DAPI) for 15 min. Finally, after rinsing with PBS, the cells were observed under confocal laser.

Figure 5:
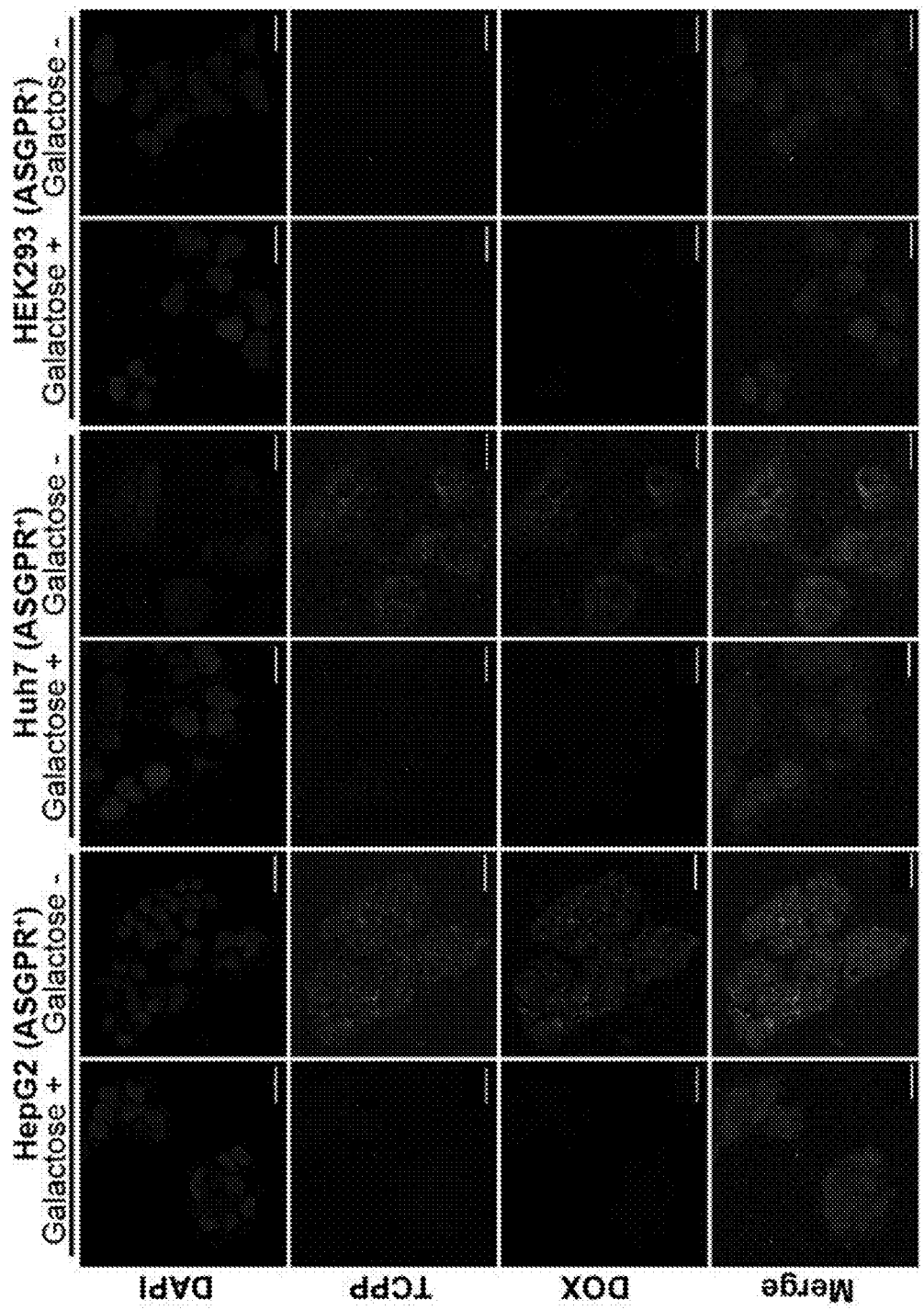
FIG. 5 shows laser confocal images of HepG2, Huh7 and HEK293 cells incubated with the inorganic nanomaterial DOX@Gal-PCN-224 with or without galactose (1 mM) competition. The scale of images is 25 μm.

It can be seen from FIG. 5 that in HepG2 and Huh7 cells, obvious fluorescence from the inorganic nanomaterials DOX and TCPP can be seen, while almost no fluorescence is observed in COS7 and HEK293 cells. Also, with the galactose competition, no fluorescence of DOX and TCPP is observed in the HepG2 and Huh7 cells. The experiment proves that the DOX@Gal-PCN-224 inorganic nanomaterial can recognize and enter the HepG2 and Huh7 cells through the galactose-asialoglycoprotein receptor.

Example 6: Verification of Capability of Drug DOX@Gal-PCN-224 of Specifically Targeting and Recognizing Asialoglycoprotein Receptors on Surfaces of Hepatoma Cells HepG2 and Huh7 by Flow Cytometry HepG2, Huh7 and HEK293 cells were inoculated in a 24-well plate at the density of $2 \times 10^5$ cells per well respectively. After culturing for 12 hours, 1 mM of galactose was added to the galactose competition group. After culturing for 24 hours, the cell density reached 90%. After the medium was removed and the cells were washed three times with PBS, the three kinds of cells were incubated with a medium containing 20 μg/mL DOX@Gal-PCN-224 for 3 hours. Then the cells were digested with pancreatin and centrifuged for 3 min at the rotating speed of 1000 rpm, supernate was discarded, and gathered cells were resuspended with PBS and then blown off. The centrifugation process was repeated three times to remove residual medium and the inorganic nanomaterial to reduce interference to fluorescence detection. Finally, the cells were dispersed with PBS and placed in a flow type tube, and fluorescence intensity of the cells in each group was detected using flow cytometry.

Figure 6:
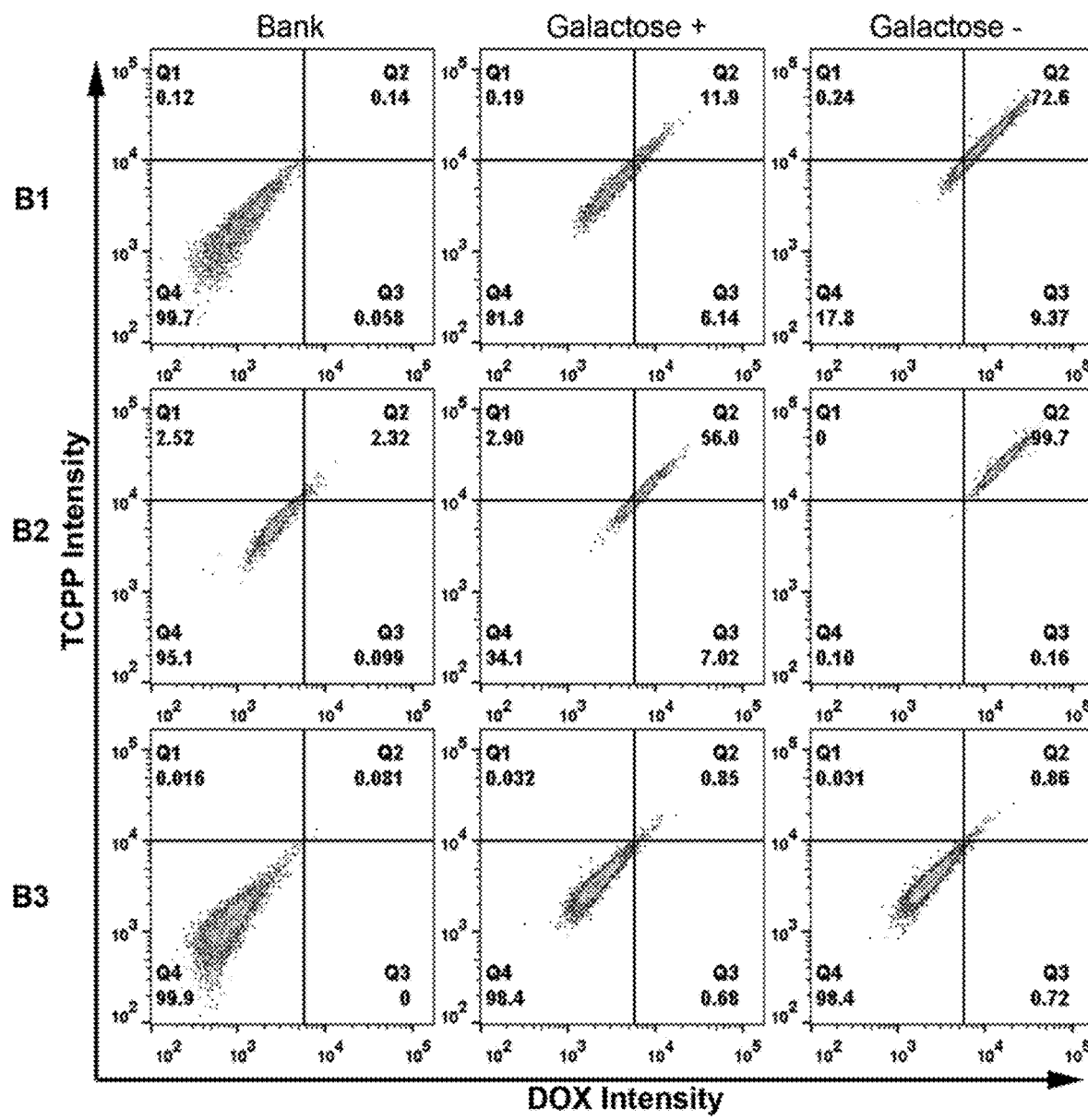
FIG. 6 shows flow cytometry of HepG2 (B1), Huh7 (B2) and HEK293 (B3) cells incubated with the DOX@Gal-PCN-224 with or without galactose (1 mM) competition. The four-quadrant diagram shows the fluorescence signals of DOX and TCPP.

As shown in FIG. 6, under different environments, the speed of the DOX@Gal-PCN-224 inorganic nanomaterial entering the HEK293 cells is basically the same and basically has no difference from the control group not treated with the DOX@Gal-PCN-224. This is due to the low expression of the asialoglycoprotein receptor on the surface of the HEK293 cells, and the inorganic nanomaterial cannot rapidly enter the cells by endocytosis targeted and mediated by the surface galactose-asialoglycoprotein receptor. However, in different environments, the speed of the DOX@Gal-PCN-224 inorganic nanomaterial entering the HepG2 and Huh7 cells is significantly different. In the case where the surface asialoglycoprotein receptor is pre-saturated, the DOX@Gal-PCN-224 inorganic nanomaterial cannot recognize the HepG2 and Huh7 cells via surface-linked galactose, and can only enter tumor cells through non-targeted endocytosis, so the fluorescence intensities of DOX and TCPP are low. However, for surface receptor-overexpressed cells, the DOX@Gal-PCN-224 inorganic nanomaterial can rapidly bind to the surface asialoglycoprotein receptors of the tumor cells via surface-linked galactose, and then enters the tumor cells via receptor-mediated endocytosis.

Example 7: Ability of Drug DOX@Gal-PCN-224 to Produce $^1O_2$

The ability of the DOX@Gal-PCN-224 to produce $^1O_2$ in living cells was evaluated using 2',7'-dichlorodihydrofluorescin diacetate (DCFH-DA). HepG2, Huh7 and HEK293 cells were incubated with the DOX@Gal-PCN-224 (20 μg/mL) for 3 hours. After the medium was removed, the cells were washed 3 times with PBS. Then the cells were incubated in a medium containing DCFH-DA (10 μM) and irradiated with a 660 nm LED light for 10 minutes. After being incubated for another 15 minutes at 37° C., the cells were washed 3 times with PBS, and a confocal microscope was used to excite and capture DCFH-DA stained fluorescent images at 488 nm. In the no light groups, except for light, the rest conditions were the same as above.

Figure 7:
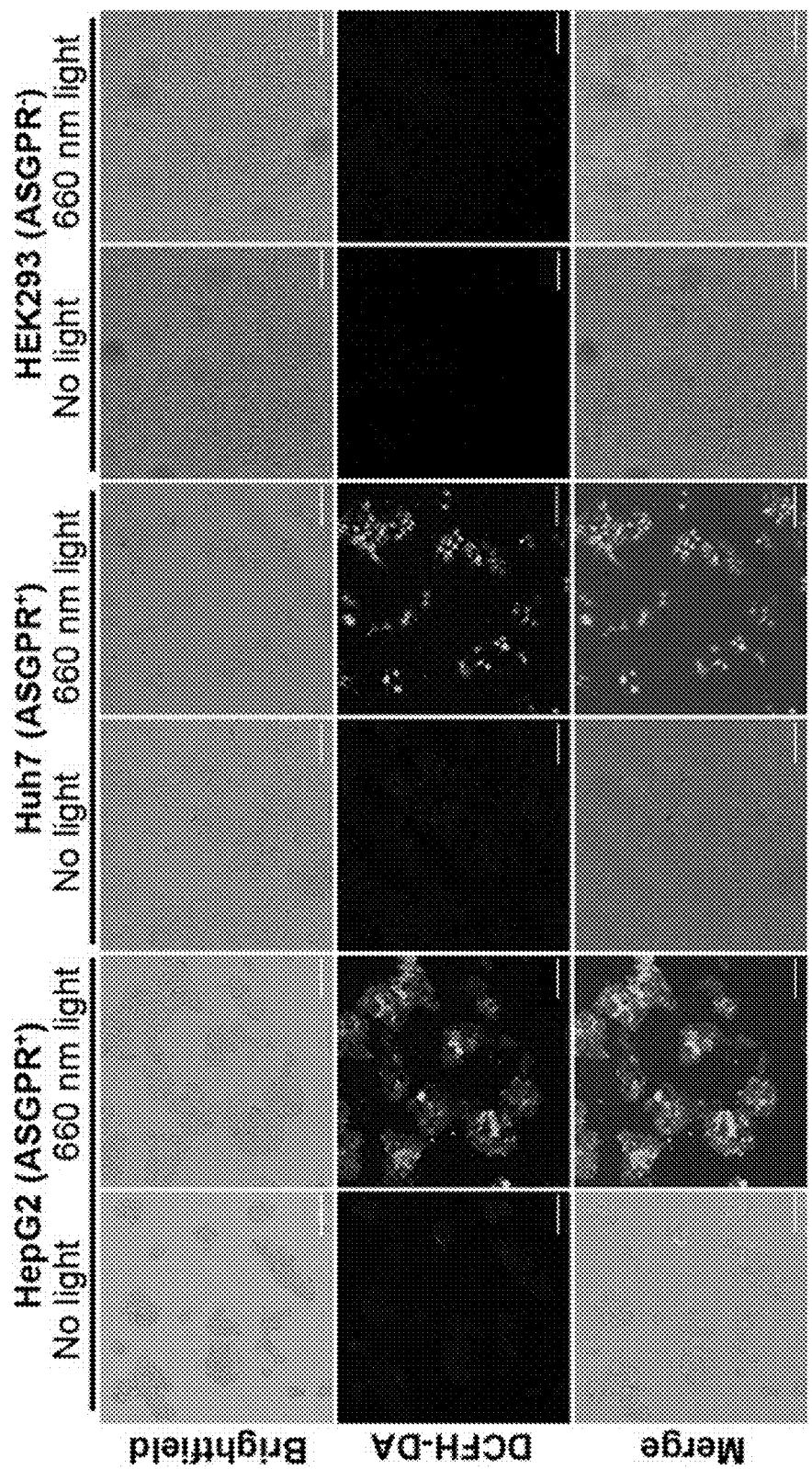
FIG. 7 shows laser confocal images generated by characterization of $^1O_2$ in the HepG2, Huh7 and HEK293 cells incubated with the DOX@Gal-PCN-224. The scale of images is 100 μm.

As can be seen from FIG. 7, HepG2 and Huh7 cells can produce $^1O_2$ after being irradiated, thus showing DCF green fluorescence. On the other hand, for HepG2 and Huh7 cells not exposed to light, only weak green fluorescence can be seen, and it indicates that without triggering by light, almost no $^1O_2$ is produced. No obvious green fluorescence can be seen in HEK293 cells regardless of whether the cells are irradiated or not. This is because only a small amount of inorganic nanomaterial enters the cells within 3 hours, and there is not enough photosensitizer to produce $^1O_2$.

Example 8: In Vitro Therapeutic Effect of Drug DOX@Gal-PCN-224

The in vitro therapeutic effect of the inorganic nanomaterial DOX@Gal-PCN-224 was detected by the live and death staining method and the corresponding MTT experiment.

Human hepatoma cells Huh7 were inoculated in a laser confocal culture dish (35 mm) at the density of $8 \times 10^4$ per well. After culturing for 24 hours, the cells were incubated with a medium containing 10 μg/mL DOX, 60 μg/mL PCN-224, 70 μg/mL DOX@PCN-224 (with the drug loading ratio of 14.2, and the DOX content of about 10 μg/mL) or 70 μg/mL DOX@Gal-PCN-224 (with the drug loading ratio of 14.2, and the DOX content of about 10 μg/mL) respectively for 24 hours. Then the light group was irradiated with a 660 nm light source for 10 min. After incubating for 24 hours, Calcein-AM/PI live and dead co-staining was performed. Finally, the cells were observed under the confocal laser. After the same treatment, the therapeutic effect of each group was further quantified by the MTT experiment.

Figure 8:
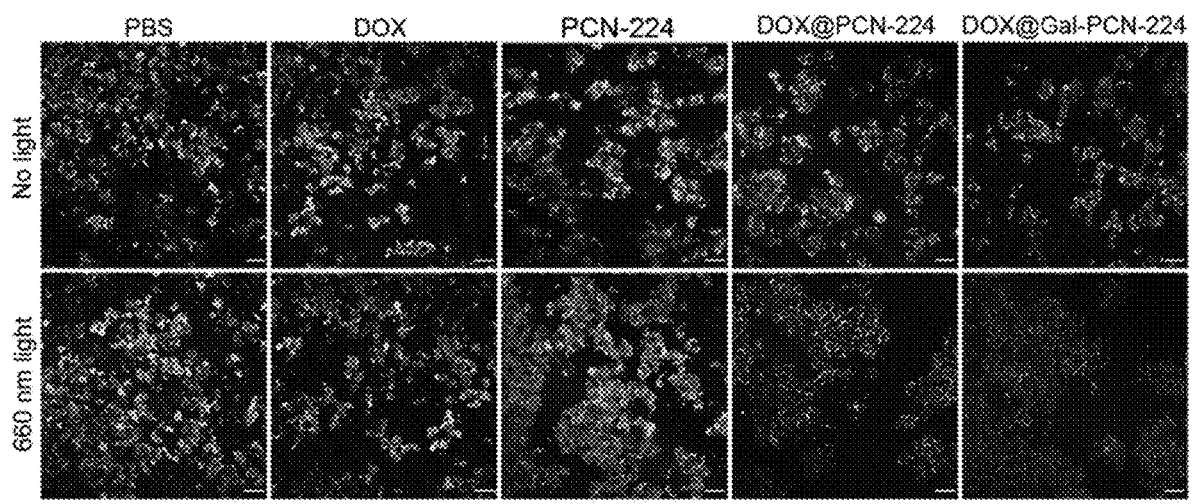
FIG. 8 shows live and dead cell staining images of Huh7 cells subjected to different treatments, the scale bar being 100 μm.

The live and dead staining laser confocal image is shown in FIG. 8. Green fluorescence indicates live cells and red fluorescence indicates dead cells. In the PBS control group, only green fluorescence is observed regardless of light, and it indicates that there is almost no apoptosis. In the DOX chemotherapy group, only sporadic red fluorescence is observed regardless of light, and it indicates that chemotherapy alone can only cause apoptosis of a small amount of Huh7 cells. In the PCN-224 photodynamic therapy group, when no light is applied, there is almost no red fluorescence observed; after the light is applied, a certain amount of red fluorescence is observed, and it indicates that some cells have apoptosis due to the photodynamic therapy. In the DOX@PCN-224 chemotherapy and photodynamic therapy synergistic treatment group, when no light is applied, some cells have apoptosis, which is caused by chemotherapy; after the light is applied, a large amount of cells have apoptosis, and it indicates that the synergistic treatment of chemotherapy and photodynamic therapy aggravates cell apoptosis. In the DOX@Gal-PCN-224 targeted chemotherapy and photodynamic therapy synergistic treatment group, when no light is applied, a large amount of cells still have apoptosis, and it reflects the effect of targeted chemotherapy; after the light is applied, almost no green fluorescence can be seen, and it indicates that almost all cells have apoptosis caused by the targeted synergistic treatment, and further shows the advantage of the targeted synergistic treatment of the disclosure.

The MTT results are shown in Table 1. The cell survival rate of each experimental group is consistent with the results of live and dead staining, and it further verifies the in vitro therapeutic effect of the inorganic nanomaterial DOX@Gal-PCN-224. The metal-organic frameworks have basically no inhibitory effect, but after loading DOX, the metal-organic frameworks can cooperate with DOX to promote the inhibitory effect.

TABLE 1

In vitro therapeutic effects of different drug treatment systems

| Treatment systems | Cell viability | Treatment systems | Cell viability |
|---|---|---|---|
| PBS | 99% | DOX@PCN-224 | 75% |
| DOX | 82% | DOX@PCN-224 + 660 nm laser | 42% |
| DOX + 660 nm laser | 79% | DOX@Gal-PCN-224 | 37% |
| PCN-224 | 97% | DOX@Gal-PCN-224 + 660 nm laser | 9% |
| PCN-224 + 660 nm laser | 63% | — | — |

Example 9: In Vivo Distribution Effect of Drug DOX@Gal-PCN-224

In order to achieve a better fluorescence imaging effect, the inorganic nanomaterials were first modified with rhodamine B (RhB), and were denoted as DOX@PCN-224-RhB and DOX@Gal-PCN-224-RhB.

To construct subcutaneous solid tumor mouse models, male BALB/c nude mice with the average weight of 14-17 g at the age of 4 weeks were inoculated with 0.1 ml of 6×10$^6$ cells/ml PBS at the right gluteus. After four weeks, when the tumor size exceeded 200 mm$^3$ (volume=0.52×tumor length× tumor width$^2$), the mice were divided into 2 groups with 5 mice in each group. The DOX@PCN-224-RhB (0.1 mL 0.4 mg/mL) and DOX@Gal-PCN-224-RhB (0.1 mL 0.4 mg/ml) were injected into the tail vein respectively. The fluorescence signal of RhB was detected by a small animal imager (Bruker In Vivo Xtreme II) at set time points (3, 6, 12, 24, 48 hours). Then the mice were sacrificed, the heart, liver, spleen, lung and kidney were isolated, and the RhB fluorescence signal of each organ was detected.

Figure 9A:
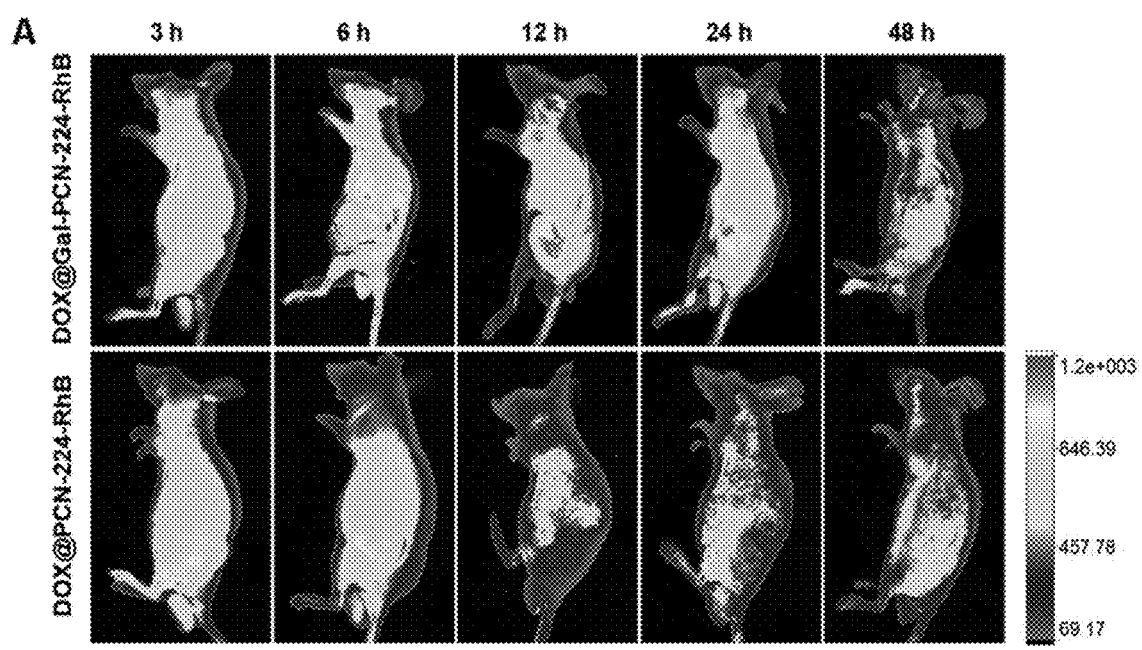
FIG. 9A-9B shows.
Figure 9B:
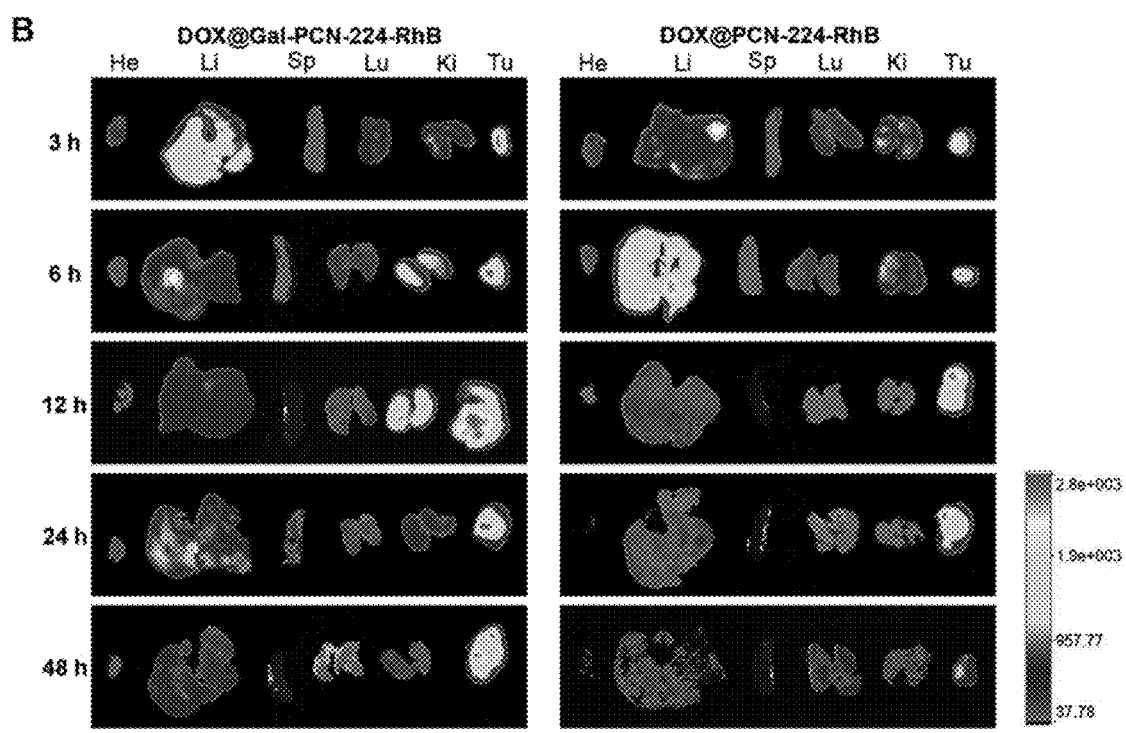

The in vivo imaging results are shown in FIG. 9A-9B. The experimental group injected with the DOX@Gal-PCN-224-RhB is named the targeted group, and the experimental group injected with the DOX@PCN-224-RhB is named the non-targeted group. It can be observed from FIG. 9A that compared with the non-targeted group, and the targeted group has a better concentration effect at the tumor site. 3 hours and 6 hours after the tail vein injection, it can be observed that the inorganic nanomaterials of both the targeted group and the non-targeted group have spread all over the mice. 12 hours and 24 hours after tail vein injection in the targeted group, more obvious fluorescence is observed at the tumor site, and it indicates that due to the targeting effect, more inorganic nanomaterials enter the tumor site. 48 hours after the tail vein injection, it is observed that the fluorescence in the whole body weakens, and it indicates that the inorganic nanomaterials are gradually metabolized during circulation in the body. FIG. 9B is an image of organs isolated at various time points, which also reflects the same trend. From this it can be concluded that the targeted inorganic nanomaterial is more likely to accumulate at the tumor site and stays longer at the tumor site.

Example 10: Inhibition of Tumor Growth in Subcutaneous Solid Tumor Mouse Models with Drug DOX@Gal-PCN-224

When the subcutaneous tumor size of the mice exceeded 50 mm$^3$, the mice were randomly divided into 9 groups with 5 mice in each group: (1) saline, (2) free DOX saline (2 mg/kg), (3) free DOX+660 nm laser (2 mg/kg), (4) PCN-224 (12 mg/kg), (5) PCN-224+660 nm laser (12 mg/kg), (6) DOX@PCN-224 (14 mg/kg), (7) DOX@PCN-224+660 nm laser (14 mg/kg), (8) DOX@Gal-PCN-224 (14 mg/kg), and (9) DOX@Gal-PCN-224+660 nm laser (14 mg/kg). The day before the first tail vein injection was set to "Day 0". At the specified time points (days 1, 4, 7, 10, 13, 16, and 19), the mice in the above experimental groups were subjected to tail vein injection. For the light groups, the tumor site was irradiated with a light source of 660 nm (20 mW/cm$^2$) for 10 minutes on the 2, 8 and 14 days. At the specified time points (days 3, 6, 9, 12, 15, 18, and 21), the tumor volume and mouse body weight of the experimental groups were measured.

Figure 10A:
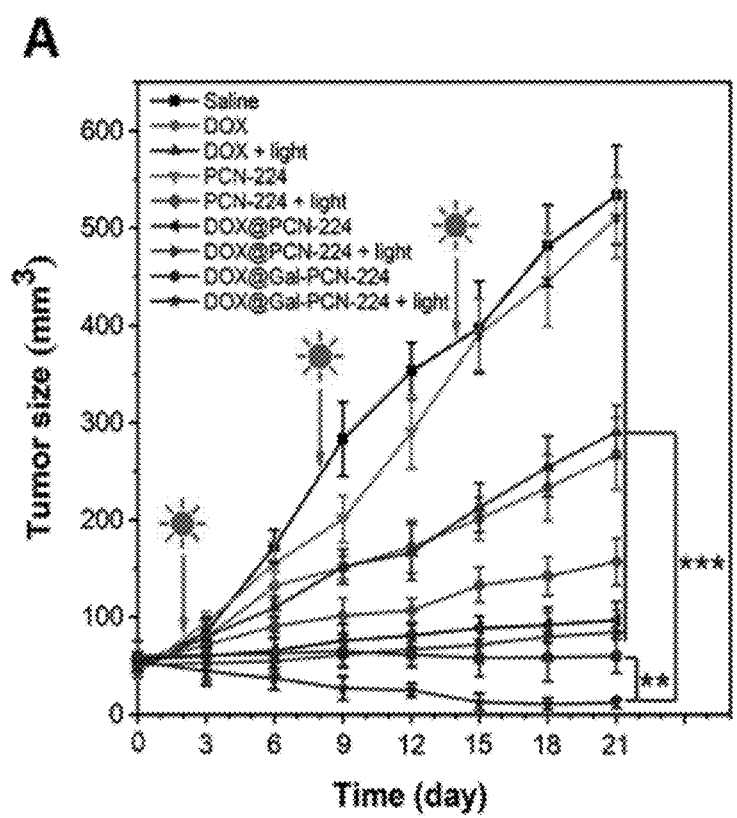
FIG. 10A-10B.
Figure 10B:
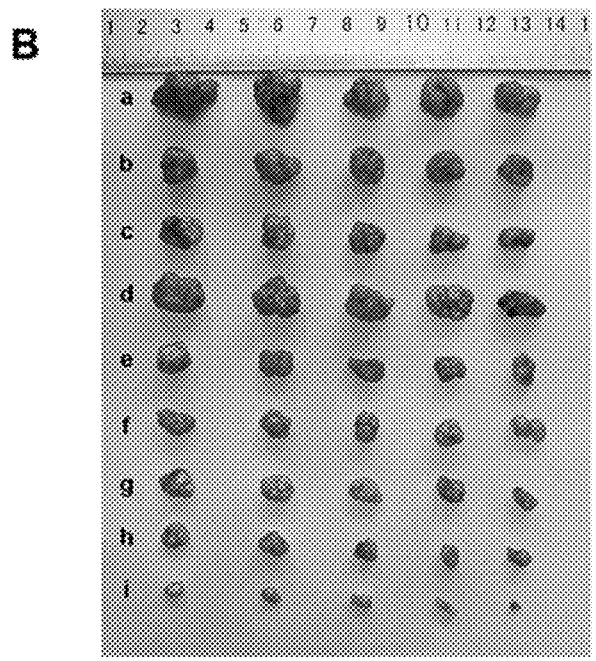

As shown in FIG. 10A-10B, the DOX@Gal-PCN-224+ 660 nm laser, DOX@Gal-PCN-224 and DOX@PCN-224+ 660 nm laser groups have good tumor growth inhibition effects. The tumor inhibition efficiency was calculated based on the tumor volume data of each group obtained on the last day of the experiment (tumor inhibition efficiency=(1− average tumor volume of the experimental group/average tumor volume of the saline control group)×100%), where the DOX@Gal-PCN-224+660 nm laser group has the highest inhibition efficiency of 97.8%. It can be concluded that DOX@Gal-PCN-224+660 nm laser can inhibit tumor growth maximally.

TABLE 2

Tumor inhibition results of different drug treatment systems

| Treatment system | Tumor inhibition efficiency | Treatment system | Tumor inhibition efficiency |
|---|---|---|---|
| DOX | 49.8% | DOX@Gal-PCN-224 | 88.8% |
| PCN-224 | 4.3% | DOX@PCN-224 + 660 nm laser | 84.1% |
| PCN-224 + 660 nm laser | 70.6% | DOX@Gal-PCN-224 + 660 nm laser | 97.8% |
| DOX + 660 nm laser | 45.5% | — | — |
| DOX@PCN-224 | 81.8% | — | — |

Example 11: Inhibition of Tumor Growth in Tumor In Situ Mouse Models with Drug DOX@Gal-PCN-224

To construct mouse models with tumor in situ, the isolated subcutaneous tumor tissue was cut into small tissue masses with the size of 2 mm×3 mm×3 mm, and the small tissue masses were placed in an inoculating needle and inoculated into the Glisson's capsule of the mouse liver. Two weeks after the tumor in situ model was constructed, the tumor in situ-bearing mice were randomly divided into 9 groups with 5 mice in each group. The groups and administration time are consistent with the subcutaneous tumor experiment, and the mouse body weight measurement time is also consistent with the subcutaneous tumor experiment. On the 11th day, a 660 nm light source was introduced to the surface of the tumor in situ using an optical fiber for irradiation for 10 min. On the 20th day, the livers of all experimental mice were subjected to $T_1$-weighted magnetic resonance imaging (Aspect Imaging, Israel).

Figure 11A:
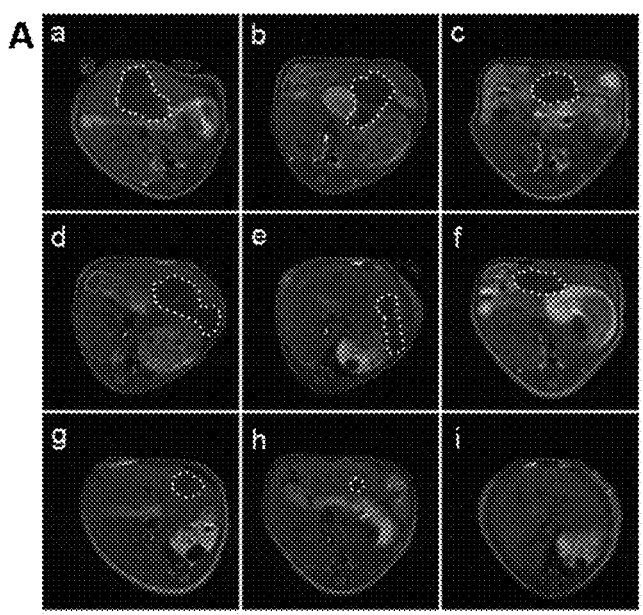
FIG. 11A-11B shows.
Figure 11B:
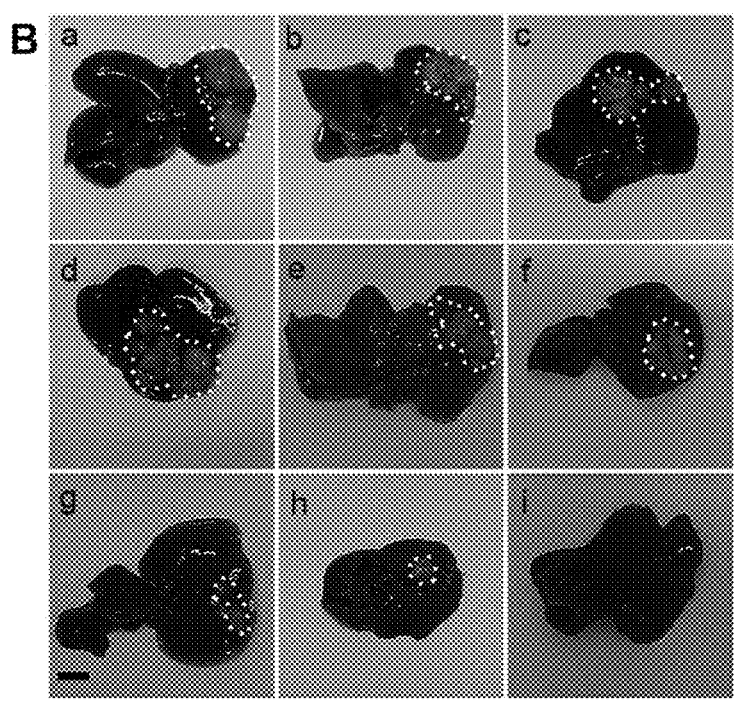
Figure 12:
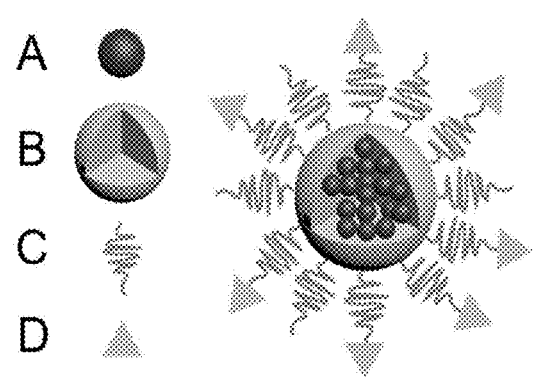
FIG. 12 shows the structure of the drug having components A, B, C and D.

As shown in FIG. 11A-11B, from the T1-weighted MRI image and the tumor in situ image, it can be seen that the tumor area can hardly be seen in the DOX@Gal-PCN-224+ 660 nm laser group, and is the smallest among all the experimental groups, and it indicates that the DOX@Gal-PCN-224+660 nm laser group has the highest tumor inhibition efficiency, and the result is consistent with the tumor inhibition effect of the subcutaneous tumor models.

What is claimed is:

1. A method for preparing a drug for targeted treatment of liver diseases, wherein the drug has a structure having components A, B, C and D;
  wherein A is selected from one or more of the same or different chemotherapeutic drugs: doxorubicin, sorafenib and 5-fluorouracil;
  B is metal-organic frameworks (MOFs) with a photosensitizer as a linking arm;
  C is a linking group, and the linking group is-CO-PEG-CO-;
  D is galactose or a monosaccharide or oligosaccharide molecule containing a galactosamine residue;
  wherein the MOFs are used as a carrier to load the chemotherapeutic drugs, and a surface of the MOFs is linked to the galactose or the monosaccharide or oligosaccharide containing the galactosamine residue through the -OCO-PEG-COO linking group;

wherein the MOFs are selected from PCN-224 and PCN-222;

wherein the method comprises the following steps:

(1) preparing chemotherapeutic drug@-PCN-224:
dispersing $ZrOCl_2 \cdot 8H_2O$, TCPP and benzoic acid in an organic solvent; mixing the materials uniformly; adding a chemotherapeutic drug to form a mixed system; performing a reaction at 80-100° C.; then performing solid-liquid separation to collect precipitate; washing and drying the precipitate to obtain chemotherapeutic drug@PCN-224; wherein the chemotherapeutic drug is selected from one or more of the following: doxorubicin, sorafenib, and 5-fluorouracil;

(2) dispersing the chemotherapeutic drug@PCN-224 obtained in step (1) and COOH-PEG-COOH in water to form a mixed solution; performing a reaction at room temperature; after the reaction, performing solid-liquid separation to collect precipitate; washing and drying the precipitate to obtain carboxyl-modified chemotherapeutic drug@PCN-224; and (3) dissolving the carboxyl-modified chemotherapeutic drug@PCN-224 obtained in step (2), amino-modified galactose, and a condensing agent in water; performing a reaction at room temperature; after the reaction, performing solid-liquid separation to collect precipitate; washing and drying the precipitate to obtain chemotherapeutic drug@Gal-PCN-224.

2. The method of claim 1, wherein a mass ratio of the chemotherapeutic drug to the $ZrOCl_2 \cdot 8H_2O$ to the TCPP to the benzoic acid in the step (1) is 1:(5-8):(2-4):(50-60).

3. The method of claim 1, wherein a concentration of the chemotherapeutic drug in the mixed system in the step (1) is 0.4-0.6 mg/mL.

4. The method of claim 1, wherein a mass ratio of the chemotherapeutic drug@PCN-224 to the COOH-PEG-COOH in the step (2) is (2-2.5):1.

5. The method of claim 1, wherein a mass concentration of the chemotherapeutic drug@PCN-224 in the mixed solution in the step (2) is 0.8-1.2 mg/mL.

6. The method of claim 1, wherein in step (3), a mass ratio of the carboxyl-modified chemotherapeutic drug@PCN-224 to the amino-modified galactose is 1:(0.5-0.8).

7. The method of claim 1, wherein the condensing agent in step (3) contains 1-(3-dimethylaminopropyl)-3-ethylcarbodiimide hydrochloride and N-hydroxysuccinimide.

8. The method of claim 7, wherein a mass ratio of the 1-(3-dimethylaminopropyl)-3-ethylcarbodiimide hydrochloride to the N-hydroxysuccinimide in the condensing agent is 1.7:1.

* * * * *